(12) United States Patent
Bertrand et al.

(10) Patent No.: US 9,500,632 B2
(45) Date of Patent: Nov. 22, 2016

(54) DEVICE FOR DETECTING AND/OR DOSING HYDROGEN AND METHOD OF DETECTING AND/OR DOSING HYDROGEN

(71) Applicant: Agence Nationale Pour La Gestation Des Dechets Radioactifs, Chatenay-Malabry (FR)

(72) Inventors: Johan Bertrand, Bievres (FR); Sylvie Delphine-Lesoille, L'Hay les Roses (FR); Xavier Pheron, Saint-Etienne (FR)

(73) Assignee: AGENCE NATIONALE POUR LA GESTION DES DECHETS RADIOACTIFS, Chatenay-Malabry (FR)

( * ) Notice: Subject to any disclaimer, the term of this patent is extended or adjusted under 35 U.S.C. 154(b) by 172 days.

(21) Appl. No.: 14/369,314

(22) PCT Filed: Dec. 26, 2012

(86) PCT No.: PCT/EP2012/076898
§ 371 (c)(1),
(2) Date: Jun. 27, 2014

(87) PCT Pub. No.: WO2013/098289
PCT Pub. Date: Jul. 4, 2013

(65) Prior Publication Data
US 2014/0374578 A1    Dec. 25, 2014

(30) Foreign Application Priority Data
Dec. 30, 2011 (FR) .................... 11 62587

(51) Int. Cl.
*G01N 33/00* (2006.01)
*G01N 21/63* (2006.01)
(Continued)

(52) U.S. Cl.
CPC .......... *G01N 33/0057* (2013.01); *G01N 21/49* (2013.01); *G01N 21/636* (2013.01); *G01N 21/94* (2013.01); *G01N 33/005* (2013.01); *G01N 2021/638* (2013.01); *G01N 2201/088* (2013.01)

(58) Field of Classification Search
CPC .......... G01N 2021/638; G01N 21/49; G01N 21/636; G01N 21/94; G01N 2201/088; G01N 33/005; G01N 33/0057
See application file for complete search history.

(56) References Cited

U.S. PATENT DOCUMENTS 6,813,403 B2 * 11/2004 Tennyson .......... G01D 5/35383
250/227.11

FOREIGN PATENT DOCUMENTS

EP    1195628    4/2002
EP    1426804    6/2004
(Continued)

OTHER PUBLICATIONS

Yibing Zhang et al: "Applications of optical fiber sensors in the oil refining and petrochemical industries", 2011 ISSS Sensors Proceedings: Limerick, Ireland, Oct. 28-31, 2011,Piscataway, NJ, Oct. 28, 2011, pp. 346-349.
(Continued)

*Primary Examiner* — Francis M Legasse, Jr.
(74) *Attorney, Agent, or Firm* — Pearne & Gordon LLP (57) ABSTRACT

The invention concerns a device (100) for the detection and/or quantitative analysis of hydrogen, intended for monitoring an installation (1). Said device (100) comprises a first measuring optical fiber (10) intended to equip the installation (1), and an optical system (20) optically connected to the first measuring optical fiber (10) and adapted to measure the variation in at least one parameter of the first measuring optical fiber (10). The optical system (20) is adapted to measure the parameter along the first optical fiber (10) according to the principle of Brillouin measurement. The invention also concerns a method using such a device (100).

16 Claims, 6 Drawing Sheets

(51) Int. Cl.
*G01N 21/49* (2006.01)
*G01N 21/94* (2006.01)

(56) References Cited

FOREIGN PATENT DOCUMENTS

| EP | 2 362 190 A1 | 8/2011 |
|---|---|---|
| JP | 61 017048 A | 1/1986 |
| WO | WO2008136870 A2 | 11/2008 |
| WO | 2009/067671 A1 | 5/2009 |
| WO | 2010/009951 A1 | 1/2010 |
| WO | 2011/022829 A1 | 3/2011 |
| WO | WO2011115683 A2 | 9/2011 |

OTHER PUBLICATIONS

International Search Report for PCT/EP2012/076898 dated Mar. 4, 2013.
Written Opionion for PCT/EP2012/076898.
French Search Report for FR 1162587 dated Jul. 3, 2012.

* cited by examiner

DEVICE FOR DETECTING AND/OR DOSING HYDROGEN AND METHOD OF DETECTING AND/OR DOSING HYDROGEN

TECHNICAL FIELD

The invention relates to the field of the detection and quantitative analysis of hydrogen.

Installations such as storage premises, geothermal drillings, warehousing sites and industrial tanks of chemical and/or radioactive products may be subject to risks of release of hydrogen related to the products stored, these releases of hydrogen are explosive and may under certain conditions be harmful for humans.

To control these risks and to preventatively detect any release of hydrogen that might take place, it is common to equip this type of storage premises with chemical detectors suitable for detecting and/or measuring hydrogen. Because of the long storage periods (several years) of chemical or radioactive products and the inaccessibility of the storage structures, the associated instrumentation and chemical detectors, such as hydrogen detectors, for obvious reasons of safety, must be durable over time, that is to say have optimum stability and sensitivity throughout all or part of the storage period. They must in addition be deployed in large numbers in order to cover large areas and characterise non-homogeneous environments. Finally, the measuring device must take into account the aspects of the risks of explosions and must be able to guarantee intrinsic safety of the device.

The invention therefore relates more specifically to a device for the detection and/or quantitative analysis of hydrogen, and to a method for the detection and/or quantitative analysis of hydrogen.

PRIOR ART

When it is a case of monitoring the presence of hydrogen in installations such as storage sites for chemical and/or radioactive products, having areas to be monitored with an extent that exceed around a hundred metres, the use is known of devices for the detection and/or quantitative analysis of hydrogen using an optical fibre as a hydrogen sensor. This type of device has, among other advantages, that of providing detection guaranteeing the intrinsic safety of the installation since it uses an optical measurement without risk of sparks that might trigger an explosion in a gaseous environment containing a large quantity of hydrogen.

Below and in the rest of this document hydrogen means hydrogen in its atomic form, in its molecular form (that is to say dihydrogen) or in its isotope form, i.e. deuterium.

Thus the document WO 2009/067671 describes such a device for the detection and/or quantitative analysis of hydrogen. The device described in the document WO 2009/067671 comprises:
- a measuring optical fibre intended to equip the installation in the area to be monitored,
- an optical system optically connected to the optical fibre and suitable for measuring the variation in the absorption of light by said optical fibre at a clearly defined wavelength.

Such a device uses the property of diffusion of hydrogen in an optical fibre and deterioration of the transition properties at certain wavelengths that result therefrom. This is because the absorption of hydrogen in a fibre causes the creation of a hydroxyl group OH and molecular dihydrogen $H_2$ absorbing certain wavelengths in the infrared such as at 1080, 1180 and 1240 nm. The attenuation of the transmission of the fibre at these wavelengths is therefore directly related to the concentration of hydrogen therein.

Thus, when such a device equips an installation to be monitored with the optical fibre deployed over the whole of the area to be monitored, a leakage of hydrogen will give rise to an absorption of part of the hydrogen by the sensing optical fibre which can be detected by said measurement of light absorption.

Nevertheless, though such a device affords effective detection of the presence of hydrogen in the installation, it does have a certain number of drawbacks. This is because such a device is dependent on the aging of the optical fibre which, if this state is not perfectly known, may cause erroneous detection of the presence of hydrogen. This is because agings of optical fibres cause losses of transmission, usually non-homogeneous in the spectral range of near infrared, and therefore giving rise to uncertainties on the detection of hydrogen with the invention described in WO 2009/067671.

Document WO 2008/136870 describes another type of device for the detection and/or quantitative analysis of hydrogen for which the measuring optical fibre comprises at least one inscribed Bragg grating, that is to say a portion of the fibre on which the refractive index is modulated periodically, and a target coating of the part of the optical fibre that receives the Bragg grating. The target coating is suitable for the absorption of hydrogen. Such a device comprises, in a similar fashion to the device described in WO 2009/067671, the measuring optical fibre that is intended to equip the installation and an optical system optically connected to the optical fibre.

The optical system for such a device is configured so as to emit electromagnetic radiation at various wavelengths in the optical fibre and to measure the wavelength at which each inscribed Bragg grating reflects said electromagnetic radiation. This is because the characteristics of an inscribed Bragg grating are dependent on the quantity of hydrogen adsorbed by the target coating. It is therefore possible, by measuring the wavelength at which one of the Bragg gratings reflects, to determine the quantity of hydrogen adsorbed by the corresponding coating.

Thus, when such a system is put in place in an installation to be monitored, the optical fibre comprising the inscribed Bragg grating or gratings being deployed over the whole of the area to be monitored, a leakage of hydrogen close to one of the inscribed Bragg gratings causes a shift in the wavelength of the electromagnetic radiation reflected by this Bragg grating and detects the leakage at the point where it takes place.

Such a device therefore enables hydrogen to be detected in the installation at each of the inscribed Bragg gratings with, if there is multiplexing of the Bragg gratings, the possibility of identifying the geographical origin of the hydrogen leak.

Though a device as described in WO 2008/136870 makes it possible to detect the presence of hydrogen in the installation with a possibility of identifying the geographical origin of the leak, the device does have a certain number of drawbacks. This is because the optical fibre has a number of locations at which the detection and/or quantitative analysis is obtained that is limited since it is dependent on the inscription of a Bragg grating and the multiplexing technology used. It should also be noted that the aging of the target coatings, as described in WO 2009/067671, is not known and presents uncertainty as to the maintenance of the sensitivity of the product for periods greater than several years.

In addition such a device also presents risks of disappearance of the Bragg gratings because of the conditions of exposure of the optical fibre to hydrogen.

DISCLOSURE OF THE INVENTION

The present invention aims to remedy these drawbacks.

One of the aims of the invention is therefore to provide a device for the detection and/or quantitative analysis of hydrogen using an optical fibre for the detection of hydrogen that is able, when it equips the area to be monitored of an installation, to detect the presence of hydrogen and identify the location of this source of hydrogen, continuously over the entire length of the optical fibre, such a device having to present a detection and/or quantitative analysis of hydrogen that are little dependent on the state of aging of the optical fibre compared with a device of the prior art.

To this end, the invention relates to a device for the detection and/or quantitative analysis of hydrogen intended for the monitoring of an installation, said device comprising:
a first measuring optical fibre intended to equip the installation,
an optical system optically connected to the first measuring optical fibre and suitable for measuring at least one parameter of the first optical fibre,
the optical system being suitable for measuring the parameter of the first optical fibre along the first measuring optical fibre according to a measurement principle of the Brillouin type.

Thus such a device, by using the principle of Brillouin measurement for measuring a parameter of the first measuring optical fibre, makes it possible to detect a variation in the effective propagation index of the optical mode $n_{eff}$ along the first measuring optical fibre, this variation directly influencing the Brillouin peaks and therefore the parameters measured during a measurement according to the principle of measurement of the Brillouin type. The diffusion of hydrogen in an optical fibre having an effect on the effective propagation index of the optical mode $n_{eff}$, such a diffusion, by causing the variation in the refractive index, and therefore in the parameters measured according to the principle of the Brillouin measurement, is detectible and quantifiable by means of such a device.

Such a measurement, being dependent on the effective propagation index of the optical mode $n_{eff}$, unlike that dependent on the variation in the transmission of the optical fibre at a given wavelength, and being related only to a variation in the Brillouin peak, does not exhibit any marked dependency vis-à-vis the state of aging of the optical fibres. Such a device therefore enables a detection and/or quantitative analysis that are not dependent on the state of aging of the optical fibre and which therefore remain reliable over time.

This measurement, being able, according to a principle identical to the Brillouin temperature measurement along an optical fibre, performed over the entire length of the first measuring optical fibre with a spatial resolution of less than one metre over a distance greater than around ten kilometres, makes it possible to locate the precise point where the variation in the parameter takes place and therefore the precise portion of the first measuring optical fibre in which the diffusion of hydrogen took place.

Such a device therefore makes it possible, when it equips an area to be monitored of an installation, to detect and quantify a source of hydrogen with an identification of the precise location of this source in the area to be monitored, without having to anticipate the sites of these events, over long periods of times, since the measurement is only very little impacted by the aging of the measuring optical fibre.

Measuring according to the principle of a Brillouin measurement means above and in the rest of this document the measurement of at least one parameter concerning (i) the Brillouin backscatter spectrum (whether it be a case of Stokes or anti-Stokes frequencies, principal or secondary peaks, related to the various acoustic modes having a non-zero overlap with optical mode) or (ii) Brillouin gain. This parameter may for example be the offset in frequency of one of the two Brillouin backscatter peaks with respect to the electromagnetic pulse giving rise to the Brillouin backscatter phenomenon or between peaks, the intensity of one of these two Brillouin peaks or their forms (full with at half maximum of the peak for example).

Brillouin peak means, above and in the rest of this document, both a spontaneous Brillouin backscatter peak and a Brillouin gain peak, the type of peak being dependent directly on the type of Brillouin measurement made by the device when it is used. Thus, for example, for a device making a Brillouin measurement according to the principle of reflectometry.

The parameter of the first optical fibre can be measured according to a Brillouin measurement principle selected from the group of methods comprising Brillouin optical reflectometry measurement associated with a spatial resolution method by coding in the time domain, Brillouin optical reflectometry measurement associated with a method of location by coding in the frequency domain, Brillouin optical reflectometry measurement in the correlation domain, Brillouin gain optical measurement associated with an analysis in the time domain, Brillouin gain optical measurement in the frequency domain and Brillouin gain optical measurement by analysis in the correlation domain.

Thus the device can be adapted according to the requirements related to the installation to be monitored in terms of spatial resolution, the distance along which the monitoring is carried out, the hydrogen detection threshold and the quantitative hydrogen resolution.

The measurements of Brillouin optical reflectometry in the time domain, Brillouin optical reflectometry in the frequency domain, Brillouin optical reflectometry in the correlation domain, Brillouin optics by analysis in the time domain, Brillouin optics in the frequency domain and Brillouin optics by analysis in the correlation domain are better known by their English names and the corresponding abbreviations, which are respectively Brillouin Optical Time Domain Reflectometry (BOTDR), Brillouin Optical Frequency Domain Reflectometry (BOFDR), Brillouin Optical Time Domain Analysis (BOTDA), Brillouin Optical Time Frequency Domain Analysis (BOFDA) and Brillouin Optical Correlation Domain (BOCDA). These measurements are measurements that are generally implemented in optical fibre temperature measurement devices and/or in deformation monitoring devices.

The device can be adapted to make a reference measurement of at least one parameter of the measuring optical fibre at at least one location on the first measuring optical fibre, said reference measurement not being influenced by the presence of hydrogen.

In this configuration, the measurement of a parameter of the first measuring optical fibre makes it possible, for a parameter influencing the Brillouin measurement, to correct the measurement made according to the principle of the Brillouin measurement and thus to improve the detection and/or quantitative analysis of the hydrogen by limiting or even eliminating the influence of the parameter measured during the reference measurement.

The parameters influencing the Brillouin measurement may in particular be the temperature, the deformation of the first measuring optical fibre and radioactivity, pressure, relative humidity and water content of the atmosphere.

The optical system can be adapted to make the reference measurement along the first optical fibre at two or more different wavelengths. To do this, the device could contain several pump lasers or stimulate in cascade the Brillouin lines generated.

A measurement of a parameter at two different pump wavelengths for which the presence of hydrogen presents two different influences makes it possible, when this influence is known, to eliminate this influence and to provide a reference measurement of said parameter that is not sensitive to hydrogen.

The optical system can be adapted by adding other types of optical fibre placed close to the fibre measuring the hydrogen, to measure the variation of at least one other influence parameter of the measuring optical fibre, so as to provide a reference measurement of the temperature and/or the deformation and/or of the other parameters listed above along the measuring optical fibre.

The device can be adapted to make a reference measurement of at least one parameter along the first optical fibre according to other backscatter measurements, whether it be the Raman or Rayleigh diffusion principle.

The first measuring optical fibre may comprise at least one portion made insensitive to hydrogen so that the measurement of a parameter of the first measuring optical fibre by the optical system at said portion provides a reference measurement.

Above and in the rest of the document, portion of optical fibre, or optical fibre, made insensitive to hydrogen means that the portion of optical fibre, or the optical fibre, has a configuration such that the present of hydrogen in the atmospheric environment of said portion of optical fibre, or of said fibre, does not influence the measurement made on said portion of optical fibre or on said optical fibre.

Such a portion makes it possible to provide a reference measurement without influence of hydrogen to correct the measurement of the parameter of the first measuring optical fibre according to the principle of the Brillouin measurement.

A reference optical fibre can also be provided which, being intended to equip the installation, is connected to the optical system, said reference optical fibre being intended to provide a reference measurement A reference optical fibre can also be provided which, being intended to equip the installation, is connected to the optical system, said reference optical fibre being intended to provide a reference measurement of the temperature and/or of the deformation along the first measuring optical fibre.

Such a reference optical fibre, by providing a measurement of a parameter that may interfere with the hydrogen detection and/or quantitative analysis measurement according to the principle of the Brillouin measurement, makes it possible to correct said detection and/or quantitative analysis measurement along the first measuring optical fibre. Such a correction makes it possible to limit, or eliminate, the influence of the parameter measured during the reference measurement done on the reference optical fibre.

The reference optical fibre can be configured so as to have reduced sensitivity to hydrogen, preferentially so as to be made insensitive to hydrogen.

Such reduced sensitivity, or insensitivity, to hydrogen of the reference optical fibre makes it possible to reduce or even cancel the influence of the hydrogen on the reference measurement obtained by means of the reference optical fibre.

The reference optical fibre may comprise a core and a cladding the material of which is configured so that the reference optical fibre has reduced sensitivity to hydrogen, preferentially zero.

According to this possibility, the core and/or cladding may be a glass based on silicon or chalcogenide or voids filled with air or liquids ("fibres with holes").

The reference optical fibre may comprise a core and a cladding where the distribution of doping elements is configured so that the reference optical fibre has reduced sensitivity to hydrogen, preferentially zero.

The reference optical fibre may comprise a coating adapted to limit the diffusion of hydrogen in the reference optical fibre.

A second measuring optical fibre can also be provided which, being intended to equip the installation, is connected to the optical system, said second measuring optical fibre being configured so as to have an interaction with hydrogen different from that of the first measuring optical fibre.

Thus, with such a second measuring optical fibre, the device gives access to two measurements for which the interaction with hydrogen is different and makes it possible, according to said interaction difference, to provide supplementary information on the hydrogen source detected, such as temporal information or optimised sensitivity over a more extensive range than with a device having a single measuring optical fibre.

The second measuring optical fibre may comprise a means for limiting the diffusion of hydrogen in said second measuring optical fibre.

Such a means for limiting the diffusion reduces the speed at which the hydrogen will enter the optical fibre, thus providing temporal information on the source of hydrogen giving rise to the hydrogen detected.

The means for limiting the diffusion of hydrogen of the second measuring optical fibre may comprise a coating of said second measuring optical fibre, said coating have partial permeability to hydrogen.

Partial permeability to hydrogen means that the coating is adapted to limit the penetration of hydrogen into the optical fibre that is equipped with said coating, without for all that completely eliminating the diffusion in said optical fibre.

Such a coating provides a means for limiting the diffusion of hydrogen in the second measuring optical fibre, with an influence on the optical properties of the second measuring optical fibre that is low, or even zero.

The means for limiting the diffusion of hydrogen of the second measuring optical fibre may be the choice of optical fibres the internal structure of which is modified, either by the choice of its dopants, or by the choice of its glass matrix, or by prior treatments, such as a prior hydrogen load that is configured so as to increase the sensitivity to hydrogen of said second measuring optical fibre, or such as an ionising radiation load, for example gamma and/or UV radiations.

These prior treatments make it possible to change the hydrogen detection threshold and thus to change the sensitivity of the detection and/or quantitative analysis obtained from the measurements made with such a second measuring optical fibre.

These specific prior treatments and choices of optical fibres (in terms of nature and primary and secondary coatings) change the saturation threshold of the hydrogen absorption.

The second measuring optical fibre may have a prior hydrogen load configured so as to modify the interaction of said optical fibre with hydrogen.

The measuring optical fibre or fibres and the reference optical fibre may be placed in the form of a cluster or a ribbon.

Such a placement of the optical fibres with respect to one another makes it possible to offer an identical environment for all the optical fibres from the thermal point of view and from the point of view of the stresses, pressure and radiation level to which they are subjected. Thus, for a device comprising a reference optical fibre, the reference measurement is performed under conditions identical to those used for the detection and/or quantitative analysis of hydrogen. Likewise, for a device comprising a second measuring optical fibre, the measurements made by the first and second measuring optical fibres are comparable with each other.

The invention also concerns a method for the detection and/or quantitative analysis of hydrogen, for monitoring an installation, said method comprising the steps consisting of:
  installing a first measuring optical fibre in the installation,
  making a measurement of a parameter along the measuring optical fibre according to the principle of Brillouin measurement.

The invention also concerns a method for the detection and/or quantitative analysis of hydrogen using a device according to the invention and comprising the steps consisting of:
  using the optical system for measuring a parameter of the first measuring optical fibre along the first measuring optical fibre according to the principle of Brillouin measurement,
  respectively detecting and/or quantitatively analysing the hydrogen in the measuring optical fibre from the parameter measured along the measuring optical fibre according to the principle of Brillouin measurement.

Such a method makes it possible to effect a detection and/or quantitative analysis of the hydrogen in an installation whatever the extent of the area to be monitored of the installation. It also makes it possible to identify, when there is detection of the presence of hydrogen, the point, along the first measurement optical fibre, at which the detection of hydrogen took place.

A device adapted for making a reference measurement can be used, the respective step of detection and/or quantitative analysis of hydrogen comprising the sub-steps consisting of:
  using the optical system for making a reference measurement along the first measuring optical fibre,
  correcting, on the basis of the reference measurement, the measurement of the parameter of the first measuring optical fibre made along the first measuring optical fibre according to the principle of Brillouin measurement,
  respectively detecting and/or measuring the presence of hydrogen in the first measuring optical fibre from the measurement of the parameter of the first measuring optical fibre along the first measuring optical fibre according to the principle of Brillouin measurement that was corrected using the reference measurement.

A method comprising such a step of correcting the index variation measurement limits the risks of erroneous detection of a presence of hydrogen that would be related for example to a change in temperature.

BRIEF DESCRIPTION OF THE DRAWINGS

The present invention will be best understood from a reading of the description of example embodiments given purely by way of indication and in no way limitatively, referring to the accompanying drawings, on which.

Identical, similar or equivalent parts of the various figures bear the same numerical references so as to facilitate passage from one figure to another.

The various parts shown in the figures are not necessarily shown to a uniform scale, in order to make the figures more legible.

The various possibilities (variants and embodiments) must be understood as not being exclusive of one another and may be combined with one another.

DETAILED DISCLOSURE OF PARTICULAR EMBODIMENTS

Figure 1:
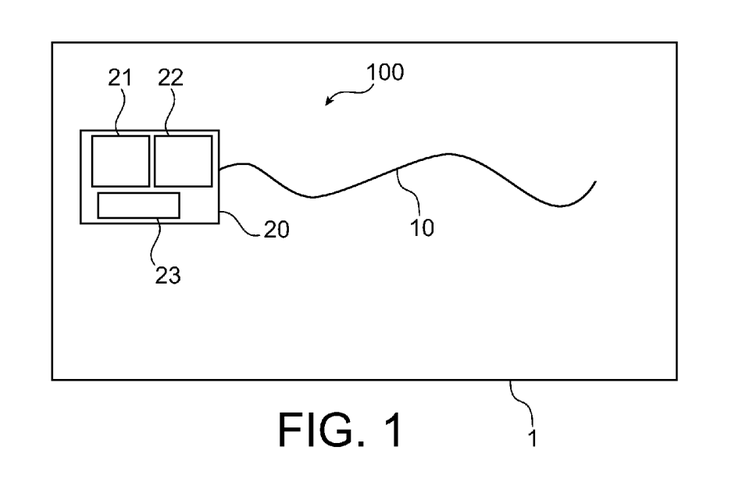
FIG. 1 illustrates schematically a device according to the invention in which a single measuring optical fibre is provided, said system comprising an optical system adapted to make a reflectometry measurement according to the Brillouin principle.

FIG. 1 illustrates a device 100 for the detection and/or quantitative analysis of hydrogen equipping an area to be monitored of an installation 1, such as storage site, a geothermal drilling, a storage site or an industrial tank for chemical and/or radioactive products. The device 100 illustrated in FIG. 1 is a device according to a first embodiment of the invention. FIG. 1 illustrates a first possibility of this first embodiment in which the configuration of the device is adapted to make a Brillouin measurement according to the reflectometry principle.

Such a device 100 comprises:
a first measuring optical fibre 10 equipping the installation 1,
an optical system 20 connected to the first measuring optical fibre 10 and adapted to make a Brillouin measurement.

It should be noted that, in the device according to the configuration illustrated in FIG. 1, the optical system is adapted for a measurement in reflectometry configuration, the optical fibre being connected to the system by only one of its ends.

The first measuring optical fibre 10 is an optical fibre adapted to the working wavelength of the optical system 20. The optical fibre may for example be similar to those generally used for making Brillouin temperature measurements.

For installations having reduced accessibility, the first optical fibre is preferentially adapted to allow a durable and stable measurement that may exceed several tens of years, without requiring any maintenance.

The first measuring optical fibre 10 comprises conventionally a core, an optical cladding and a protective coating. The core and the cladding may be made from silicon dioxide, the core having a higher refractive index than that of the cladding so as to confine the light in the core. Monomode optical fibres with an index gradient are also suitable. The change in refractive index may be obtained by incorporating doping elements conventionally used for this type of application, for example of the germanium, phosphorus, fluorine, aluminium etc. type. The coating may be adapted to the operating conditions in order to limit damage to the first measuring optical fibre 10 that might be related to the conditions in which the first measuring optical fibre 10 is installed. Such a coating, for an installation not having conditions prejudicial to the first measuring optical fibre 10, is for example a simple plastic coating such as acrylates or polyimides.

The coating of the first optical fibre may also be a coating specifically adapted to increase the sensitivity to hydrogen, for example a palladium coating. The optical fibre may also consist of specific glasses, for example glasses based on chalcogenides. "Fibres with holes" (produced by leaving voids—optionally subsequently filled in) are also suitable.

The first measuring optical fibre 10 is suitable for guiding the electromagnetic radiation at the wavelengths at which the optical system 20 emits.

The first measuring optical fibre 10 may have an adaptation so that the Brillouin backscatter spectrum, or Brillion gain, is easily measurable, by modifying the proportion of doping element along its radium. With such an adaptation, the first measuring optical fibre 10 may in particular have the various acoustic modes giving rise to Brillouin lines are spectrally separate or change in a substantially identical manner with the diffusion of hydrogen in the optical fibre.

To limit the influence of the forces applied to the first measuring optical fibre 10, the first measuring optical fibre 10 may be equipped with floating intermediate sheath (also known by the English term "loose tube") so as to reduce the forces to which the first measuring optical fibre 10 is subjected. In this way the influence that such forces could have on the detection of hydrogen is limited.

The first measuring optical fibre 10 is deployed in the installation over an area to be monitored. This deployment is carried out so as to cover the maximum surface area of the area to be monitored and thus guarantee detection of any leakage or release of hydrogen in said area.

The first measuring optical fibre 10 comprises first and second ends, the first end being connected to the optical system 20 for a Brillouin measurement of the reflectometry type in a configuration as illustrated in FIG. 1.d.

The optical system 20 is an optical system suitable for making a Brillouin measurement in a spatially resolved manner along the first measuring optical fibre.

The optical system is adapted according to the type of Brillouin measurement. Thus, in the configuration illustrated in FIG. 1, the optical system is adapted to make a Brillouin reflectometry measurement such as the Brillouin optical time domain reflectometry measurement (English abbreviation BOTDR), Brillouin optical frequency domain reflectometry measurement (English abbreviation BOFDR) and Brillouin optical correlation domain reflectometry measurement (BOCDR).

To this end, the optical system 20 comprises:
a light-emission means 21, such as a laser, suitable for emitting at least one electromagnetic radiation,
an optical measuring means 22 suitable for detecting and measuring electromagnetic radiation, such as a spectral analysis system, a gain analysis system or a loss analysis system, and
a control and analysis means 23, suitable for controlling the emission means and the measuring means, and for analysing the measurements made the measuring means 22.

The emission means 21 generally comprises a laser the wavelength of which may be fixed or tuneable according to the possibilities of the invention. The means, according to the Brillouin measurement type, may comprise one or more lasers that emit continuously or in pulses. Among this or these lasers, one laser is said to be principal, also referred to as pump, and emits a principal radiation at a principal wavelength.

For the applications sought, the principal emission wavelength of the emission means is a wavelength conventionally used for measuring temperature according to the principle of Brillouin temperature measurement. For the purpose of obtaining maximum sensitivity to the presence of hydrogen, the principal emission wavelength may be chosen in a wavelength range to which the diffusion of hydrogen presents maximum sensitivity, such as those that are mentioned in the international application WO 2009/067671. According to this principle, the emission wavelength may be approximately 1.2 µm.

The measuring means 22 is suitable for detecting and/or measuring an electromagnetic radiation at a wavelength very close to that emitted by the emission means typically close to around 10 GHz and generally between 9 and 13 GHz. Such a measuring means 22 is suited to the type of Brillouin measurement. Thus, for example, for an optical system suitable for making a BOTDR measurement, the measuring means is a spectral analysis system. Since this type of measuring means 22 is moreover known for Brillouin optical-fibre temperature sensors, it is not described in further detail in this document.

The control and analysis means 23 is suitable for controlling the emission means 21 and the measuring means 22 so as to make a measurement of a parameter of the first measuring optical fibre 10 according to the Brillouin measurement principle. The control and analysis means 23, with such adaptation, is able to control the emission means 21 so as to emit suitable electromagnetic radiation and to control the measuring means 22 so as to detect and measure the electromagnetic radiation issuing from the Brillouin phenomenon, whether it be Brillouin backscatter, gain or loss, which takes place along the first measuring optical fibre 10 when the electromagnetic radiation passes.

Since such an adaptation of the control and analysis means 23 is identical to that used during a temperature measurement by an optical fibre sensor of the Brillouin type, it is not explained in any more detail in this document.

The control and analysis means 23 is also suitable for analysing the measurements made by the detection means 22 so as to identify a potential diffusion of hydrogen at a point on the first measuring optical fibre in order to detect a variation in the effective propagation index of the optical mode $n_{eff}$ at a point on this same optical fibre 10.

According to a possibility of the invention in which the installation has a temperature that can vary locally or globally, such a variation being able to cause a variation in the Brillouin measurement along the first measuring optical fibre 10, the device can be adapted to measure a parameter at at least one location on the first measuring optical fibre 10 so as to provide a reference measurement, this reference measurement preferably being a measurement of temperature and/or deformation of the first measuring optical fibre 10.

According to this possibility, such a measurement, in order to serve as a reference measurement, must not be influenced by the presence of hydrogen. Such a condition may for example be obtained using a temperature measurement along the first optical fibre using a measurement using two different emission wavelengths of the emission means 22, by means of a measurement that may be other than a Brillouin measurement such as the one that is described in the document WO 2011/115686.

According to this same possibility, the first measuring optical fibre 10 may have portions regularly distributed over its entire length that are made insensitive to hydrogen and serve to supply the reference measurement for correcting the measurement along the portions of the first measuring fibre 10 that are not made insensitive to hydrogen. The portions that are made insensitive may be so made either by a modification to the configuration of the optical fibre in itself, in accordance with the principle described in the document EP 1195628, or by the presence of a suitable coating on the surface of said portions, such as the one described in the document EP 1426804.

Figure 2:
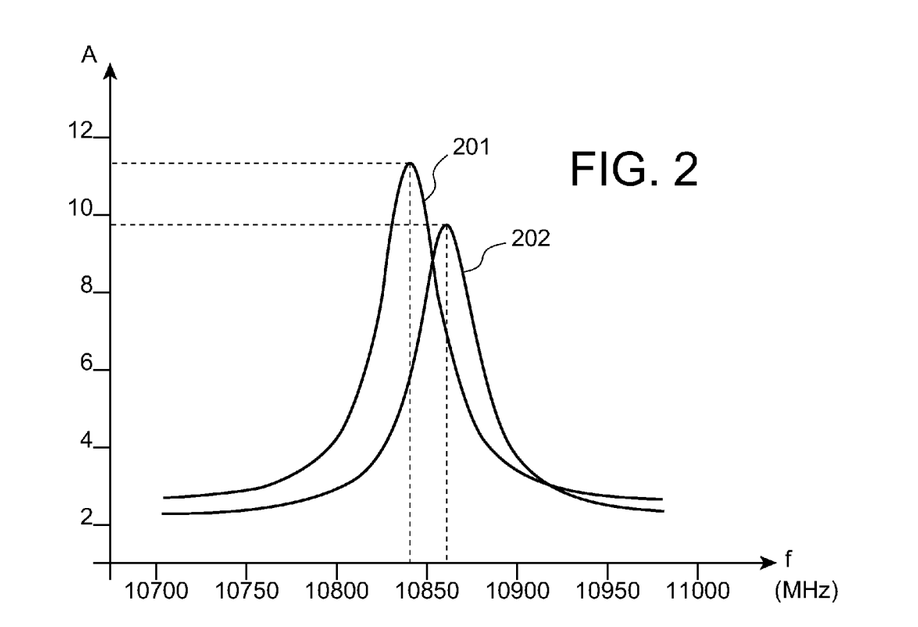
FIG. 2 illustrates two spectra of the same Brillouin backscatter peak obtained respectively using a device as illustrated in FIG. 1 respectively when the first measuring optical fibre is put in the presence of a large quantity of hydrogen and after degassing of the hydrogen from said first measuring optical fibre.

FIG. 2 illustrates an example of measurements made during the use of a device 100 according to this first embodiment. The Y axis represents the amplitude A of the intensity of the backscattered electromagnetic radiation in arbitrary units and the X axis represents the shift frequency f in the MHz of the backscattered radiation with respect to the radiation emitted by the emission means 21. During this use of the device 100, the first measuring optical fibre 10 has been put in the presence of a high hydrogen pressure (150 bar) for a period of 7 days so as to saturate the optical fibre with hydrogen. Then the first measuring optical fibre 10 has been returned to air for the same period so that the hydrogen degasses out of the first measuring optical fibre 10. The first spectrum 202 and the second spectrum 201, illustrated in this figure, were produced respectively at the end of the 7 days of exposure and at the end of the period of putting back in air.

Thus the first spectrum 202 shows a frequency shift of the Brillouin backscatter peak corresponding to a saturation with hydrogen of the first measuring optical fibre 10 while the second spectrum 201 corresponds to the Brillouin backscatter peak observed in the absence of hydrogen in said first measuring optical fibre 10.

It is thus possible to see in this figure that, when the first measuring optical fibre 10 is put in contact with hydrogen, the hydrogen diffusion causes an increase in the Brillouin frequency and a decrease in the intensity of this same peak. This dual influence is directly related to the change in the effective propagation index of the optical mode $n_{eff}$ that occurs in the Brillouin frequency shift in accordance with the following formula $$v_B = \frac{2n_{eff} V_a}{\lambda}$$

with $v_B$ the Brillouin shift frequency, $V_a$ the velocity of the acoustic waves, that is to say of the phonons giving rise to the Brillouin backscatter phenomenon, and $\lambda$ the wavelength of the electromagnetic radiation emitted.

The measurements presented in FIG. 2 illustrate the various possibilities of adapting the control and analysis means in order to detect and/or evaluate a variation in the effective propagation index of the optical wave $n_{eff}$. This is because the detection and/or evaluation of the variation in the refractive index may be obtained either:
 a) by a direct measurement of the variation in the Brillouin frequency of the principal peak or the secondary peaks,
 b) by a measurement of the intensity of the Brillouin peak of the principal peak or of one of the secondary peaks,
 c) by a measurement of intensity at a predetermined frequency corresponding substantially to that of the principal Brillouin peak or to one of the secondary peaks in the absence of hydrogen, in accordance with the latter possibility the drop in intensity will be related both to the frequency shift and to the reduction in intensity of the Brillouin peak.

Figure 3:
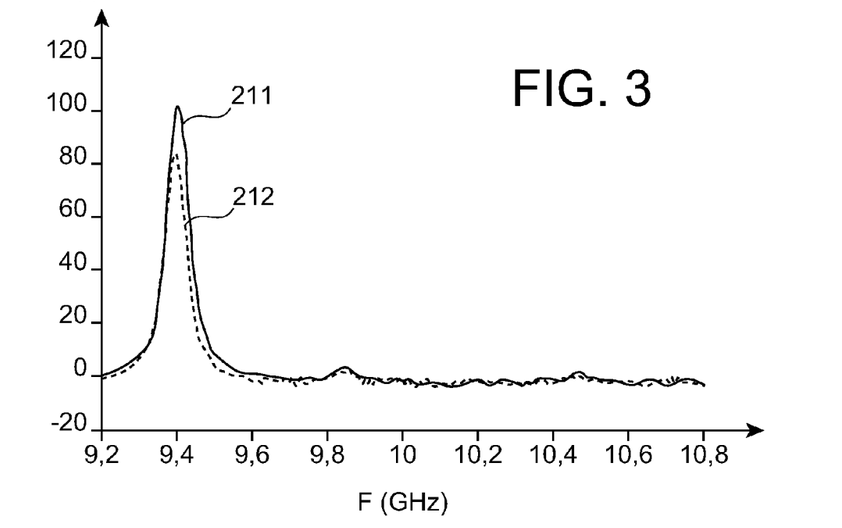
FIG. 3 illustrates two Brillouin measurement spectra both having two same Brillouin peaks, these two spectra having been obtained respectively with a device as illustrated in FIG. 1, this respectively before and during an exposure of the first measuring optical fibre of the device to an atmosphere containing 32% hydrogen.
Figure 4:
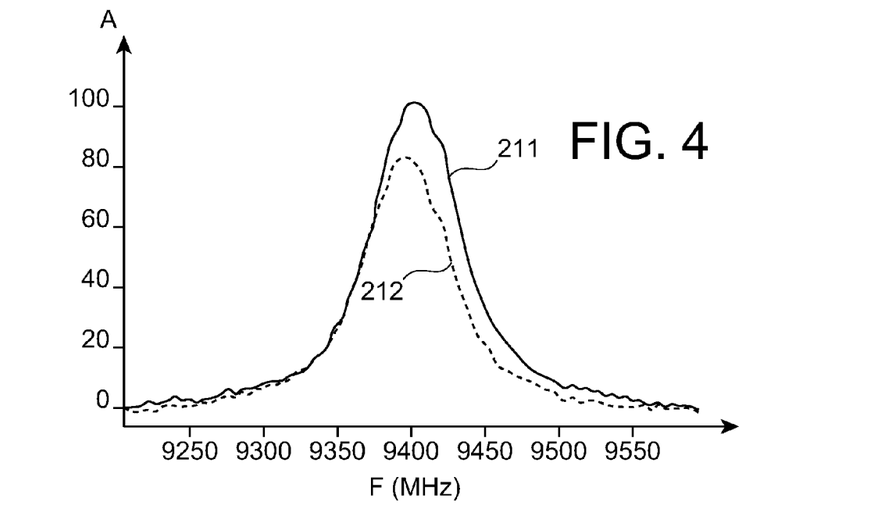
FIG. 4 illustrates a close-up view centred on the main Brillouin peak of the spectra present in FIG. 3.
Figure 5:
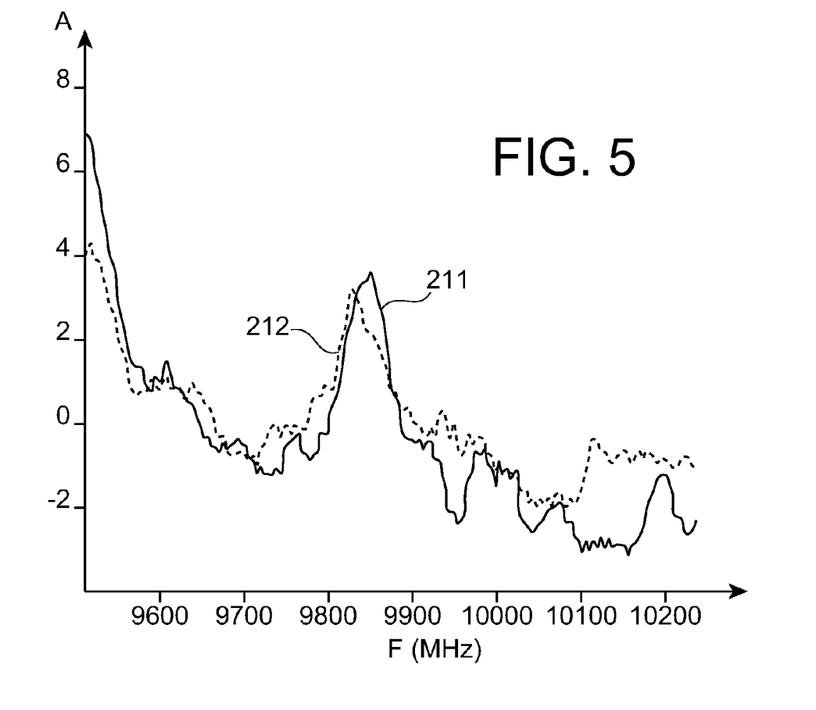
FIG. 5 illustrates a close-up view centred on the secondary Brillouin peak of the spectra present in FIG. 3.

FIG. 3 and the close-up views of the latter that are present in FIGS. 4 and 5 illustrate the possibility of functioning both on the principal Brillouin peak and on the secondary Brillouin peak. FIGS. 4 and 5 are close-up views of FIG. 3 centred on the frequency of respectively the principal and secondary Brillouin peaks.

In FIGS. 3 to 5, the Y axis represents the amplitude A of the intensity of the backscattered electromagnetic radiation in arbitrary units and the X axis represents the frequency f, this in GHz for FIG. 3 and in MHz for FIGS. 4 and 5, of the backscatter radiation with respect to the radiation emitted by the emission means 21.

The measurements that appear in FIGS. 3 to 5 are two measurements 211 and 212 of the Brillouin type obtained when the first measuring optical fibre 10 is put in contact with an atmosphere containing respectively 32% and 0% hydrogen. It can thus be seen that, during this putting of the first measuring optical fibre 10 in contact with hydrogen, that the diffusion of hydrogen causes a shift and variation in intensity on both the main and secondary Brillouin peaks. Thus the measuring system 22 can be adapted to perform a Brillouin measurement either on the principal peak or on one of the secondary peaks, or both on the principal peak and one or more of the secondary peaks.

Thus, after the installation is equipped with a device, the detection and/or quantitative analysis of hydrogen are performed in accordance with a method comprising the steps consisting of:
using the optical system to measure a variation in a parameter of the first measuring optical fibre 10 along the first measuring optical fibre 10 in accordance with the principle of Brillouin measurement,
detecting and/or quantitatively analysing the hydrogen in the first measuring optical fibre 10 using the measurement according to the principle of Brillouin measurement along the first measuring optical fibre 10.

For an optical system adapted to make a reference measurement, the step consisting of measuring and/or detecting the presence of hydrogen in the first measuring optical fibre 10 comprises the sub-steps consisting of:
using the optical system to make the reference measurement along the first measuring optical fibre 10,
correcting the measurement of variation in the parameter of the measuring optical fibre 10 along the first measuring optical fibre 10 on the basis of the reference measurement,
detecting and/or quantitatively analysing the hydrogen in the first measuring optical fibre 10 using the measurement of the parameter according to the principle of corrected Brillouin measurement along the first measuring optical fibre 10.

In the step of using the optical system for making the reference measurement, said measurement can be made simultaneously with the measurement of variation in the effective index of propagation of the optical mode $n_{eff}$ along the first measuring optical fibre 10 if the reference measurement is obtained by means of portions of the first measuring optical fibre 10 made insensitive to hydrogen.

It should be noted that, for a precise measurement of the quantity of hydrogen absorbed at a location on the optical fibre, it is also necessary to provide a prior step of calibrating the device 100.

Figure 6:
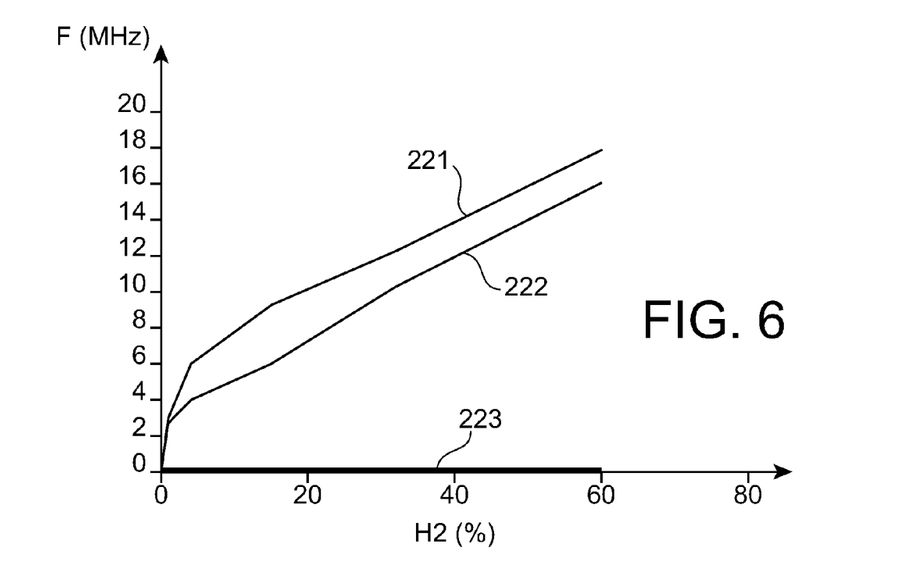
FIG. 6 illustrates the variation in the frequency of the main peak with the proportion of atmospheric hydrogen during the Brillouin measurement with a device as illustrated in FIG. 1, for two types of first measuring optical fibre and for an optical fibre made insensitive to hydrogen.

FIG. 6 is an example illustrating such a step for three different optical fibres, a first one comprising a doping based on fluorine, a second comprising a doping based on germanium and a third, as will be seen subsequently, that has been made insensitive to hydrogen.

In FIG. 6, the Y-axis represents the shift frequency f in MHz of the backscattered radiation with respect to the radiation emitted by the emission means 21 and the X-axis represents the quantity of hydrogen to which the optical fibre has been subjected.

Thus it can be seen in FIG. 6 that the two optical fibres, if they exhibit a variation in the frequency shift of the Brillouin principal peak of similar general appearance, these two fibres do not have an identical interaction with hydrogen demonstrating, for the obtaining of a precise measurement of the quantity of hydrogen with a device according to the invention, the need for such a calibration step. In addition, the measurements present in FIG. 6 also show the non-linearity of the variation in a parameter measured in accordance with a Brillouin measurement with the quantity of hydrogen to which the optical fibre is subjected.

Since such a calibration step is accessible to persons skilled in the art, it is not described in any more detail in this document.

Figure 7:
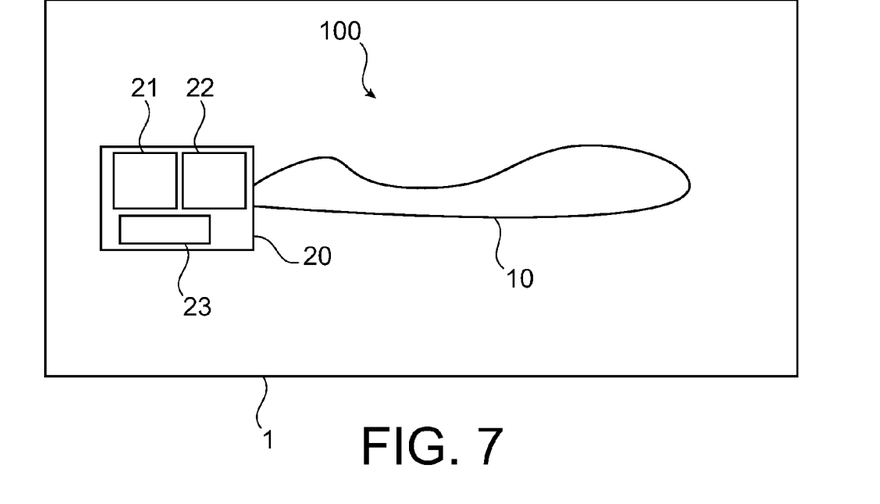
FIG. 7 illustrates a device according to the invention in which a single measuring optical fibre is provided, said system comprising an optical system adapted to make an optical analysis measurement according to the Brillouin principle.

FIG. 7 illustrates a device 100 according to a second possibility of the first embodiment in which the configuration of the device 100 is adapted to make a Brillouin measurement that is performed by analysis in the time, frequency or correlation domain.

Such a configuration is adapted for a device making the measurement of the parameter according to the principle of Brillouin measurement which is a Brillouin optical time domain analysis (BOTDA) measurement, a Brillouin optical frequency domain analysis (BOFDA) measurement or a Brillouin optical correlation domain analysis (BOCDA) measurement.

A device according to this second possibility of the first embodiment is differentiated from a system according to the first possibility in that the first measuring optical fibre 10 is connected to the optical system by both ends to enable analysis of the electromagnetic radiation emerging from the optical fibre. The optical fibre 20 has a configuration similar to that of an optical system of an optical fibre temperature sensor making the Brillouin measurement by analysis in the corresponding domain (that is to say time, frequency or correlation).

As for a device having a configuration according to the first possibility, a portion of the first optical fibre can be made insensitive to hydrogen. Such a portion is advantageously the second half of the first measuring optical fibre. Thus it is possible, by installing the second part of the first measuring optical fibre 10 along its first part, to make the reference measurement over the entire length of the first part of the first measuring optical fibre 10.

Figure 8:
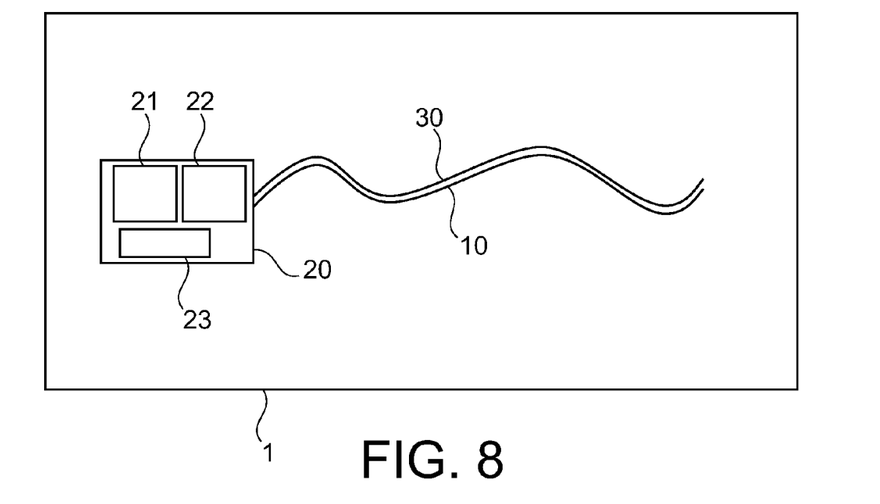
FIG. 8 illustrates a device according to a second embodiment of the invention in which the device comprises a measuring optical fibre and a reference optical fibre, the optical system being adapted to make a reflectometry measurement according to the Brillouin measurement principle.

FIG. 8 illustrates a device according to a second embodiment in which a reference optical fibre 30 is provided. FIG. 8 illustrates a first possibility of the second embodiment in which the configuration of the device is adapted to make a Brillouin measurement according to the reflectometry principle.

A device according to the second embodiment is differentiated from a device according to the first embodiment in that it comprises a reference optical fibre 30 connected to the optical system and in that the optical system 20 is adapted to make a reference measurement along the reference optical fibre 30.

According to the first possibility of this second embodiment, the reference optical fibre 30 is an optical fibre configured so as to have reduced sensitivity to hydrogen. Such a configuration of the reference optical fibre 30 can be obtained either by a modified configuration of the fibre in itself, in accordance with the principle described in the document EP 1195628, or by the presence of a suitable coating on the surface of the reference optical fibre, such as the one described in the document EP 1426804.

The reference optical fibre 30 preferentially has, to facilitate the correction of the measurement of variation in effective propagation index of the optical mode $n_{eff}$ along the first measuring optical fibre 10, characteristics similar to those of the first measuring optical fibre 10.

The first measuring optical fibre 10 and the reference optical fibre 30 are, when the installation is equipped with the device, installed side by side. To facilitate such equipping of the installation, the first measuring optical fibre 10 and the reference fibre 30 can be placed in the form of a cluster of fibres or in the form of a ribbon.

The reference optical fibre 30 is connected by one end to the optical system.

The optical system 20 is preferentially adapted to make a measurement, referred to as the reference measurement, of the variation in the parameter according to the Brillouin measurement along the reference optical fibre 30 under conditions identical to the measurement of the parameter according to the Brillouin measurement along the first measuring optical fibre 10. It is also possible, without departing from the scope of the invention, for the optical system to be adapted to measure a parameter along the reference optical fibre 30, such as temperature, so as to correct the variations in the parameter measured along the measuring optical fibre 10 according to the Brillouin measurement principle that are solely related to this parameter measured along the reference optical fibre 30.

According to the possibility of the invention in which the first reference optical fibre is equipped with a floating intermediate sheath, the reference optical fibre can also be equipped with such equipment.

The use of a device according to this second embodiment is similar to that of a device according to the first embodiment, which comprises the steps of using the optical system 20 for making the reference measurement and the correction measurement of the parameter along the first measuring optical fibre 10.

Figure 9:
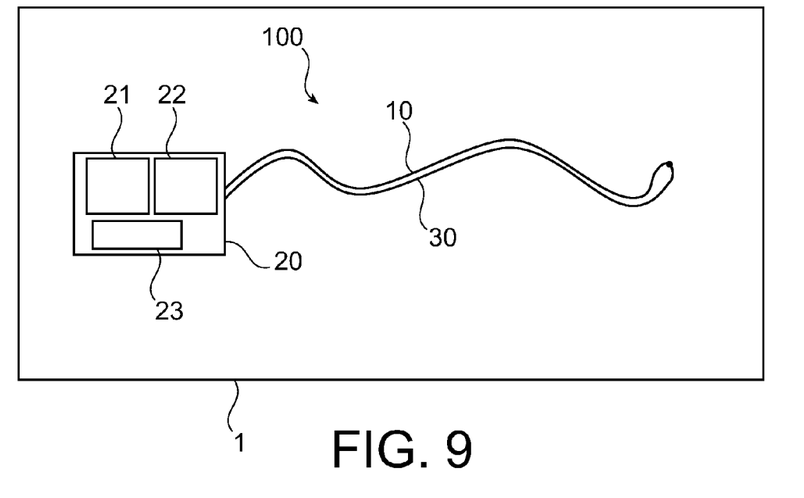
FIG. 9 illustrates a device according to a second embodiment of the invention in which the device comprises a measuring optical fibre and a reference optical fibre connected to each other, the optical system being adapted to make an analysis measurement according to the Brillouin measurement principle along the loop formed by the measuring optical fibre and the reference optical fibre.
Figure 10:
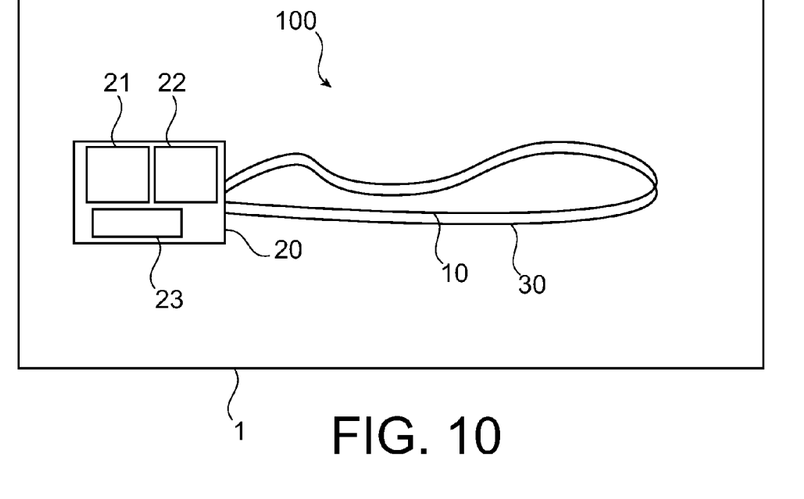
FIG. 10 illustrates a device according to a second embodiment of the invention in which the device comprises a measuring optical fibre and a reference optical fibre each connected independently to the optical system, the optical system being adapted to make an analysis measurement according to the Brillouin measurement principle along the measuring optical fibre and the reference optical fibre.

FIGS. 9 and 10 illustrate respectively a second and third possibility of the second embodiment in which the configuration of the device 100 is adapted to make a Brillouin measurement that is done by analysis in the time, frequency or correlation domain.

Such second and third possibilities of the second embodiment are differentiated from the first possibility of a system according the second embodiment in that the first measuring optical fibre 10 is connected to the optical system 20 by both ends so as to enable analysis of the radiation emerging from the optical fibre. The optical system 20 has a configuration similar to that of an optical system of an optical fibre temperature sensor making the Brillouin measurement by analysis in the corresponding domain (that is to say time, frequency or correlation).

FIG. 9 illustrates the possibility according to which the first measuring optical fibre 10 is optically coupled, by its end that is not connected to the optical system 20, to an end of the reference optical fibre 30. The end of the reference optical fibre that is not connected to the first measuring optical fibre is connected to the optical system 20. Thus this gives a configuration similar to that of the second possibility of the first embodiment for which the second part of the optical fibre was made insensitive to hydrogen.

FIG. 10 illustrates the third possibility of the second embodiment for which the first measuring optical fibre 10 and the reference optical fibre 30 are connected independently of each other to the optical system 10. The optical system, as for the first possibility of the second embodiment, is adapted to independently make the measurement of the parameter along the first measuring optical fibre 10 and the reference measurement by means of the reference optical fibre 20.

Figure 11:
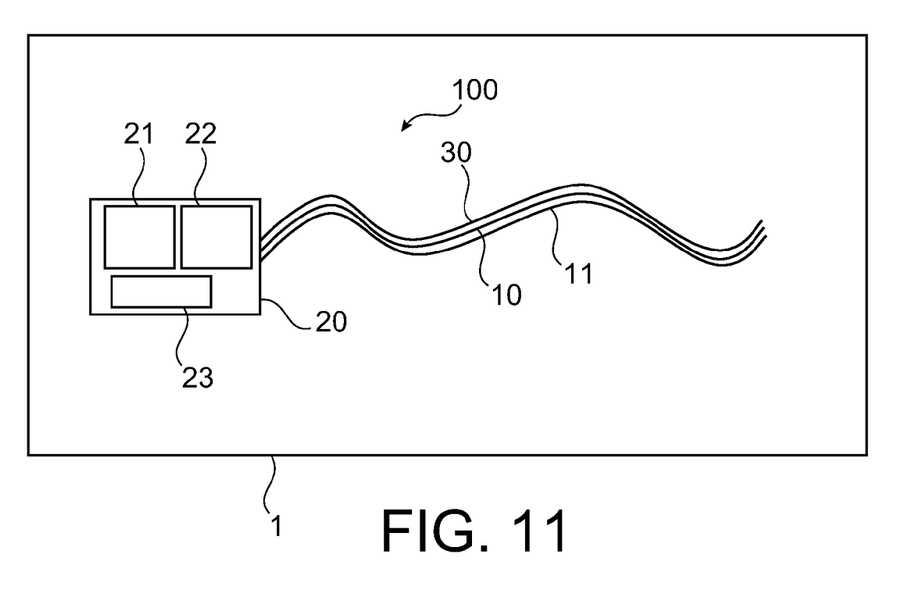
FIG. 11 illustrates a device according to a third embodiment of the invention in which the device comprises first and second measuring optical fibres and a reference optical fibre, the optical system being adapted to make a reflectometry measurement according to the Brillouin measurement principle along the first and second measuring optical fibres and the reference optical fibre.

FIG. 11 illustrates a device according to a third embodiment in which the device comprises a second measuring fibre 11.

The device 100, as illustrated in FIG. 11, and in a similar manner to the first possibilities of the first and second embodiments, has a configuration suitable for making a Brillouin measurement according to the reflectometry principle.

A device according to the third embodiment is differentiated from a device according to the second embodiment in that it comprises a second measuring optical fibre 11 having an interaction with hydrogen different from that of the first measuring optical fibre 10. The optical system is furthermore adapted to make a measurement of a parameter according to the Brillouin measurement along the second measuring optical fibre 11, this parameter being identical to that measured along the first measuring optical fibre 10.

The second measuring optical fibre 11 has a different interaction to hydrogen that may be of various types.

A first type of interaction different from the first measuring optical fibre 10 is a reduced diffusion of hydrogen in the second measuring optical fibre 11. Such an interaction may be obtained by means of a diffusion barrier such as a suitable coating of the second measuring optical fibre 11 having partial permeability to hydrogen. Such a coating may be a coating of carbon the characteristics of which, such as the thickness and density, are chosen so as to provide a reduction in the diffusion of hydrogen in the second measuring optical fibre 11 without totally eliminating it. The effect of such a coating can be seen in FIG. 6, which shows that the frequency shift 223 of the Brillouin peak for an optical fibre made insensitive to hydrogen by means of such a coating is constant and is not impacted by the presence of hydrogen.

The second type of interaction different from the first measuring optical fibre 10 is a reduced sensitivity of the second measuring optical fibre 11 to hydrogen. Such reduced sensitivity of the second measuring optical fibre 11 can be obtained with a configuration of the second measuring optical fibre 11 that is different from that of the first measuring optical fibre 10. Such a difference in configuration is for example a modified composition of the core and/or cladding of the optical fibre as described by the document EP 1195628.

Naturally, and contrary to what is described in EP 1195628, the compositions of these various parts of the second measuring optical fibre 11 are adapted so that said optical fibre 11 has a non-zero sensitivity to hydrogen. It should also be noted that, according to the same principle, it can also be envisaged increasing the sensitivity of the second measuring optical fibre to hydrogen by the use of a configuration thereof that is different.

A third type of different interaction is the variation in effective propagation index of the optical mode $n_{\mathit{eff}}$ for the same quantity of hydrogen, obtained for example by compacting the material forming the core and cladding of the optical fibre (for example silica). This third type of different interaction can also be obtained by a preloading of the second measuring optical fibre 11 with hydrogen or deuterium, this preloading being made definitive by, for example, an ultraviolet radiation treatment.

Thus, for the same quantity of hydrogen absorbed by the first measuring optical fibre and the second measuring optical fibre 11, the second measuring optical fibre 11 has a variation in effective index of the optical propagation that is equivalent to that of the preloading with hydrogen to which the quantity of absorbed hydrogen is added. Since the variation in effective propagation index of the optical mode $n_{eff}$ is not linear as illustrated in FIG. 6, the second measuring optical fibre 11 will as a result, according to the quantity of hydrogen absorbed, have a different sensitivity.

Thus the second measuring optical fibre 11, having an interaction with hydrogen different from that of the first measuring optical fibre 10, makes it possible to provide a measurement complementary to that supplied by the first measuring optical fibre 10.

In the case where the second measuring optical fibre 11 has a sensitivity different from the first measuring optical fibre 10, whether it be through its configuration or through a pre-charging with hydrogen, the device then has a range over which the hydrogen can be detected and/or quantitatively analysed that is extended by combining the ranges offered by the first and second measuring optical fibres 10, 11.

In the case where the second measuring optical fibre 11 has a reduction in the diffusion of hydrogen, this difference causes a reduced diffusion rate of the hydrogen in said second measuring optical fibre 11. The result is a difference in the measurement between the first and second measurement optical fibres 10, 11 making it possible to obtain time information on the source of hydrogen in the installation.

Naturally, according to this third embodiment, it is possible to combine these various types of difference in interaction between the first and second measuring optical fibres 10, 11 by adapting them to the conditions of installation of the device.

It is also possible, according to a principle similar to that of the third embodiment, to combine more than two measuring optical fibres so as either to enable the device to have a greater range on which the hydrogen can be detected and/or quantitatively analysed, or to combine the advantages of the various types of interaction with hydrogen.

Naturally, such an embodiment, though it is illustrated in FIG. 11 for a possibility according to which the configuration of the device is adapted to make a Brillouin measurement according to the reflectometry principle, also has the possibility, not illustrated, according to which the configuration of the device 100 is adapted to make a Brillouin measurement that is performed by analysis in the time, frequency or correlation domain. According to this possibility, the first and second measuring optical fibres 10, 11 and the reference optical fibre 30 can be coupled to the optical system parallel to each other, in series or any hybrid combination in which two optical fibres from the first and second measuring optical fibres 10, 11 and the reference optical fibre 30 are put in parallel, the third optical fibre being individually coupled to the optical system 20.

According to a possibility that is not illustrated, it is also possible for the reference optical fibre 10 to be adapted to make a measurement of parameters other than temperature and/or the deformation of the optical fibre, such as the radioactivity present in the installation, without departing from the scope of the invention. Such a measurement may enable the device to have a function of monitoring this other parameter in addition to its prime function, which is the detection and/or quantitative analysis in the installation to be monitored.

It should also be noted that each of the transmission means 21 and measuring means 22 may comprise one or more modules, a module being able to be dedicated to the measurement on a single optical fibre, whether this be reference or measuring, several optical fibres or all the optical fibres, without departing from the scope of the invention.

The invention claimed is:

1. A device for the detection and/or quantitative analysis of hydrogen intended for monitoring of an installation, the device comprising:
   a first measuring optical fibre intended to equip the installation,
   an optical system optically connected to the first measuring optical fibre and suitable for measuring at least one parameter of the first measuring optical fibre,
   wherein the optical system is configured for measuring the parameter of the first measuring optical fibre along the first measuring optical fibre according to a measurement principle of the Brillouin type and for providing a detection and/or a quantitative analysis of the hydrogen in the first measuring optical fibre from the parameter measured along the first measuring optical fibre.

2. The device according to claim 1, in which the measurement of the parameter of the first measuring optical fibre is measured according to a Brillouin measurement principle selected from the group comprising Brillouin optical reflectometry measurement in the time domain, Brillouin optical reflectometry measurement in the frequency domain, Brillouin optical reflectometry measurement in the correlation domain, Brillouin optical measurement by analysis in the time domain, Brillouin optical measurement in the frequency domain and Brillouin optical measurement by analysis in the correlation domain.

3. The device according to claim 1, in which the device is adapted to make a reference measurement of at least one parameter of the first measuring optical fibre at at least one location on the first measuring optical fibre, the reference measurement not being influenced by the presence of hydrogen.

4. The device according to claim 1, in which the optical system is adapted to make the reference measurement along the first measuring optical fibre at two different wavelengths.

5. The device according to claim 1, in which a reference optical fibre is also provided which, being intended to equip the installation, is connected to the optical system, the reference optical fibre being intended to supply a reference measurement.

6. The device according to claim 1, in which a second measuring optical fibre is also provided which, being intended to equip the installation, is connected to the optical system, the second measuring optical fibre being configured so as to have an interaction with hydrogen different from that of the first measuring optical fibre.

7. Method for the detection and/or quantitative analysis of hydrogen characterised in that it uses a device according to claim 1 and comprising the steps consisting of:
   using the optical system for measuring a parameter of the first measuring optical fibre along the first measuring optical fibre according to the principle of Brillouin measurement,
   respectively detecting and/or quantitatively analysing the hydrogen in the first measuring optical fibre from the parameter measured along the first measuring optical fibre according to the principle of Brillouin measurement.

8. The device according to claim 3, in which the first measuring optical fibre comprises at least one portion made insensitive to hydrogen so that the measurement of a parameter of the first measuring optical fibre by the optical system at the portion supplies a reference measurement.

9. The device according to claim 5, in which the reference optical fibre is configured so as to have reduced sensitivity to hydrogen, preferably so as to be made insensitive to hydrogen.

10. The device according to claim 8, wherein the second measuring optical fibre comprises a means for limiting the diffusion of hydrogen in said second measuring optical fibre.

11. The device according to claim 6, wherein the means for limiting the diffusion of hydrogen of the second measuring optical fibre comprises a cladding of said second measuring optical fibre, said cladding have partial permeability to hydrogen.

12. The device according to claim 9, wherein the second measuring optical fibre has a prior hydrogen load configured so as to modify the interaction of the second measuring optical fibre with hydrogen.

13. The device according to claim 8, in which the optical measuring fibre or fibres and the reference optical fibre are placed in the form of a cluster or ribbon.

14. The device according to claim 5, in which the optical measuring fibre or fibres and the reference optical fibre are placed in the form of a cluster or ribbon.

15. Method for the detection and/or quantitative analysis of hydrogen, for monitoring an installation, said method comprising the steps consisting of:

installing a first measuring optical fibre in the installation, making a measurement of a parameter along the first measuring optical fibre according to the principle of Brillouin measurement, respectively detecting and/or quantitatively analysing the hydrogen in the first measuring optical fibre from the parameter measured along the first measuring optical fibre according to the principle of Brillouin measurement.

16. Method according to claim 15, in which the respective detection and/or quantitative analysis step comprising the sub-steps consisting of:

using the optical system for making a reference measurement along the first measuring optical fibre, correcting, on the basis of the reference measurement, the measurement of the parameter of the first measuring optical fibre made along the first measuring optical fibre according to the principle of Brillouin measurement, respectively detecting and/or measuring the presence of hydrogen in the first measuring optical fibre from the measurement of the parameter of the first measuring optical fibre along the first measuring optical fibre according to the principle of Brillouin measurement that was corrected using the reference measurement.

* * * * *

UNITED STATES PATENT AND TRADEMARK OFFICE
CERTIFICATE OF CORRECTION

PATENT NO. : 9,500,632 B2
APPLICATION NO. : 14/369314
DATED : November 22, 2016
INVENTOR(S) : Bertrand et al.

It is certified that error appears in the above-identified patent and that said Letters Patent is hereby corrected as shown below:

In the Specification

Column 15, Line 55: please delete "fibre is" and replace it with -- fibre 10 is --

Column 16, Line 50: please delete "fibre to" and replace it with -- fibre 11 to --

Signed and Sealed this
Twenty-eighth Day of February, 2017

Michelle K. Lee
*Director of the United States Patent and Trademark Office*